United States Patent
Wu et al.

[11] Patent Number: 5,893,046
[45] Date of Patent: *Apr. 6, 1999

[54] REAL TIME MONITOR OF REACTING CHEMICALS IN SEMICONDUCTOR MANUFACTURING

[75] Inventors: Benjamin Wu, Hsinchu; Shou I. Lu, Hsin-Chu, both of Taiwan

[73] Assignee: Taiwan Seimconductor Manufacturing Company, Ltd., Hsin-Chu, Taiwan

[*] Notice: This patent issued on a continued prosecution application filed under 37 CFR 1.53(d), and is subject to the twenty year patent term provisions of 35 U.S.C. 154(a)(2).

[21] Appl. No.: 668,793

[22] Filed: Jun. 24, 1996

[51] Int. Cl.$^6$ .................................................. G01N 21/90
[52] U.S. Cl. .................... 702/22; 369/528.01; 216/60
[58] Field of Search .................... 364/498, 496, 364/497, 528.01; 73/23.37, 23.2; 156/625.1, 626.1; 216/58, 59, 60; 356/432, 436–439, 441, 442; 702/23–25, 22

[56] References Cited

U.S. PATENT DOCUMENTS

| | | | |
|---|---|---|---|
| 4,211,486 | 7/1980 | Magnussen et al. | 356/328 |
| 4,620,284 | 10/1986 | Schnell et al. | 364/498 |
| 5,014,217 | 5/1991 | Savage | 364/498 |
| 5,097,130 | 3/1992 | Koashi et al. | 250/339 |
| 5,262,961 | 11/1993 | Farone | 364/500 |
| 5,401,664 | 3/1995 | Larson et al. | 436/173 |
| 5,500,076 | 3/1996 | Jerbic | 156/626.1 |
| 5,536,359 | 7/1996 | Kawada et al. | 156/626.1 |
| 5,638,172 | 6/1997 | Alsmeyer et al. | 356/301 |

*Primary Examiner*—Melanie A. Kemper
*Attorney, Agent, or Firm*—George O. Saile; Stephen B. Ackerman; Graham S. Jones, II

[57] ABSTRACT

A method and apparatus provide for monitoring and controlling a chemical process with a chemical substance adapted for treatment of a semiconductor device. The chemical substance is held in a container. The process of monitoring is provided by transmitting a light or other electromagnetic energy from a source located within the container through the chemical substance. The electromagnetic energy transmitted through the chemical substance is sensed with a photosensor or a photosensor fiber located within the container. A comparison to a standard is made of the result of the sensing by spectrum analysis, with a passband filter between the source and the photosensor. The sensor may comprise a wavelength adjustable photosensor or a multiple wavelength photosensor.

12 Claims, 5 Drawing Sheets

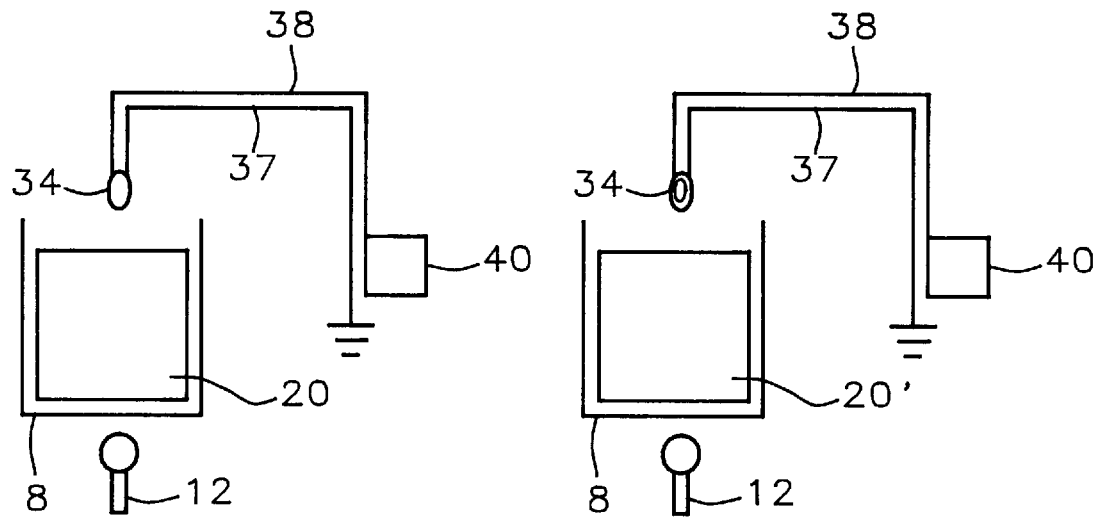
*FIG. 3A*   *FIG. 3B*
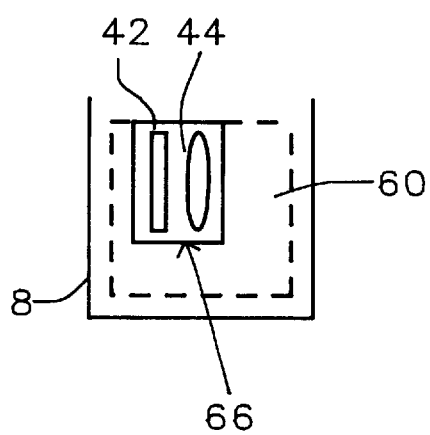 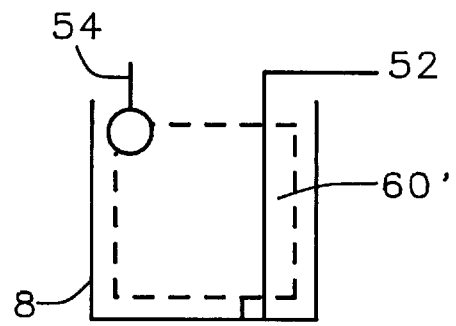
*FIG. 4A*   *FIG. 4B*

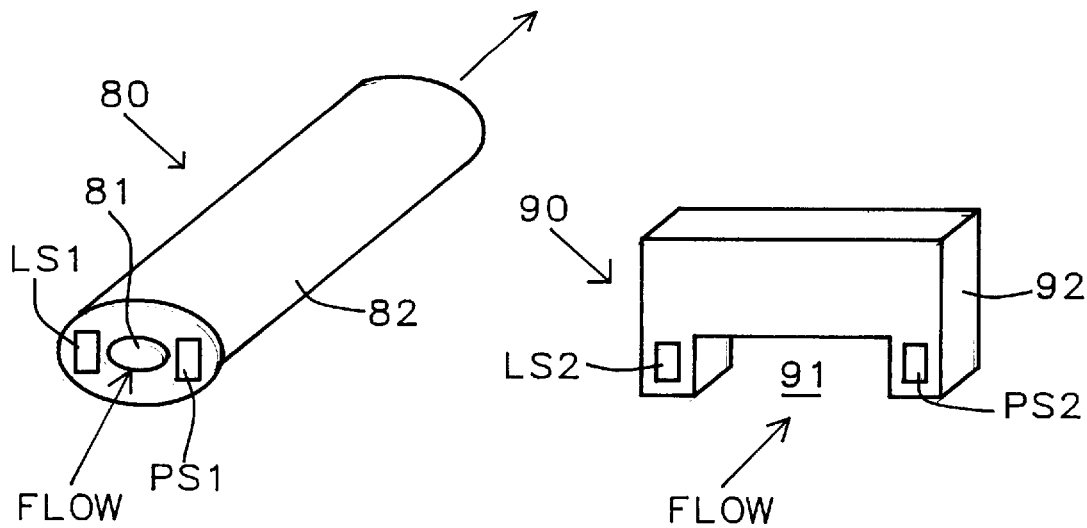
*FIG. 4C*  *FIG. 4D*
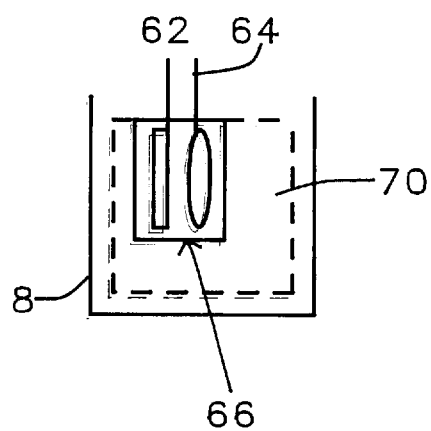  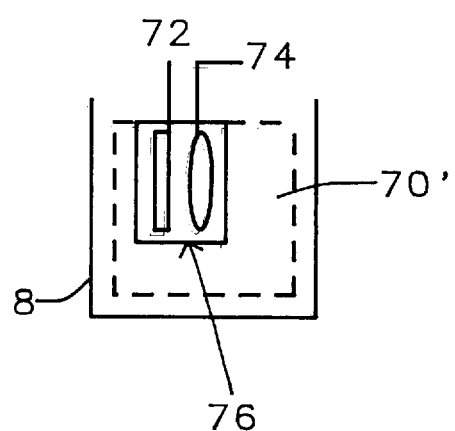
*FIG. 5A*  *FIG. 5B*

REAL TIME MONITOR OF REACTING CHEMICALS IN SEMICONDUCTOR MANUFACTURING

BACKGROUND OF THE INVENTION

1. Field of the Invention

This invention relates to a method and apparatus for monitoring and controlling a chemical process for manufacturing semiconductor devices and more particularly to detection of the condition of a chemical substance employed in such a chemical process.

2. Description of Related Art

In-line real-time testing of chemicals using density, color, spectroscopy, pH, etc. is generally known and used in many industries, including the chemical and semiconductor industries.

U.S. Pat. No. 5,262,961 of Farone for "Method for Monitoring and Controlling a Chemical Process" shows a method of monitoring and controlling a chemical process by measuring the concentration of the process reactants and products using spectrometric technology, but not in a semiconductor manufacturing process.

U.S. Pat. No. 5,401,664 of Larson et al "Analytical Method for Determining Concentration of Decomposition Products in Solvent Used for Solvent Extraction" describes an analytical method for determining the concentration of extraction. However, this invention does not appear to be a real time measurement.

Current methods of detecting the life-time of reacting chemicals are as follows:

1. Chemical analysis of contaminated elements added in the chemical, which is really time-consuming way, and is not applicable to sudden chemical variation.
2. Unscientific life-time estimate with respect to numbers of runs or lots passed through the chemical, which must be not a cost effective method.

SUMMARY OF THE INVENTION

An object of this invention is a real-time monitoring of reacting chemicals to discover a problem ahead of scheduled chemical change, or to alarm the abnormality of chemicals to minimize resultant impacts.

Another object of this invention real time monitoring of reacting chemicals using chemical life time estimation including estimation by analysis of contaminated elements in a laboratory, estimation by runs or by time and estimation by real time monitoring.

Still another object of this invention is real time monitoring of reacting chemicals by real time spectrum analysis of chemicals.

An additional object of this invention is real time monitoring assemblies for monitoring chemicals for use in real time spectrum analysis.

In accordance with this invention, a method for monitoring and controlling a chemical process includes the following steps. Place a chemical substance in a container adapted for treating semiconductor devices. Transmit electromagnetic energy from a source through the chemical substance. Sense the electromagnetic energy transmitted through the chemical substance. Compare the result of the sensing with a standard.

Preferably, sensing is provided with a wavelength adjustable photosensor and a passband filter between the source and the photosensor and the comparing comprises spectrum analysis. Sensing is provided with a multiple wavelength photosensor.

It is further preferred that sensing is provided with a multiple wavelength photosensor and the comparing comprises spectrum analysis.

Further in accordance with this invention a method for monitoring and controlling a chemical process is provided by the following steps. Place a chemical substance adapted for use in treatment of semiconductor devices in a container adapted for use in treatment of semiconductor devices. Transmit an electromagnetic energy from a source located within the container through the chemical substance. Sense the electromagnetic energy transmitted through the chemical substance with a sensor located within the container. Then, compare the result of the sensing with a standard.

Preferably, sensing is provided with a photosensor and a passband filter between the source and the photosensor and the comparing comprises spectrum analysis; and sensing is provided with a wavelength adjustable photosensor; and the comparing comprises spectrum analysis.

In accordance with another aspect of the invention, apparatus for monitoring and controlling a chemical process with a chemical substance adapted for use in treatment of semiconductor devices in a container includes means for transmitting an electromagnetic energy from a source through the chemical substance adapted for use in treatment of semiconductor devices, means for sensing the electromagnetic energy transmitted through the chemical substance, and means for comparing the result of the sensing with a standard.

Preferably, the means for sensing comprises a multiple wavelength photosensor or a wavelength adjustable photosensor and a passband filter between the source and the photosensor and the means for comparing employs spectrum analysis.

In accordance with still another aspect of this invention apparatus is provided for monitoring and controlling a chemical process. A chemical substance adapted for use in treatment of semiconductor devices is retained in a container adapted for use in treatment of semiconductor devices. Means are provided for transmitting an electromagnetic energy from a source located within the container through the chemical substance as well as means for sensing the electromagnetic energy transmitted through the chemical substance with a sensor located within the container. There are also means for comparing the result of the means for sensing with a standard. Preferably, the means for sensing comprises a photosensor and a passband filter between the source and the photosensor and the means for comparing employs spectrum analysis. Preferably, there is a wavelength adjustable photosensor or a multiple wavelength photosensor and a passband filter between the source and the photosensor.

BRIEF DESCRIPTION OF THE DRAWINGS

The foregoing and other aspects and advantages of this invention are explained and described below with reference to the accompanying drawings, in which:

FIGS. 3A and 3B show a light source and a tank similar to those of FIGS. 1A and 2A contain normal (new) chemical solution in FIG. 3A and abnormal (used) chemical solution in FIG. 3B.

FIGS. 4A and 4B show alternative kinds of photosensors and light source assemblies.

FIGS. 4C and 4D show structures of alternative types of assemblies which can be used in the arrangements such as those shown in FIGS. 4A and 4B.

FIGS. 5A and 5B show photosensors for use in accordance with this invention with different kinds of wavelengths.

DESCRIPTION OF THE PREFERRED EMBODIMENT

Figure 1A:
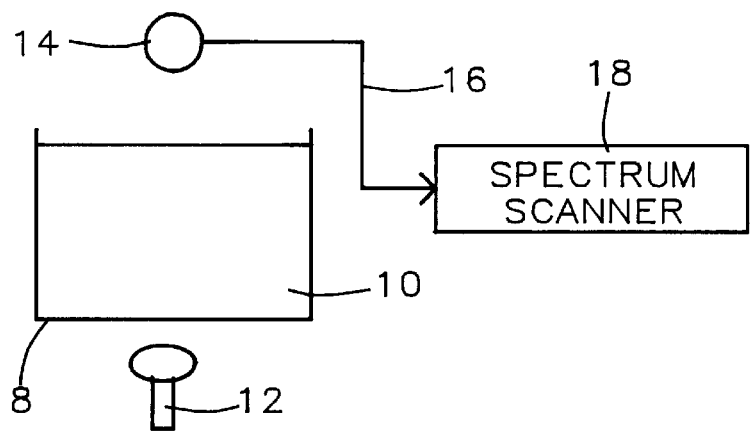
FIG. 1A shows semiconductor manufacturing apparatus with means for measuring the optical spectrum of a chemical substance.

FIG. 1A shows semiconductor manufacturing apparatus with means for measuring the optical spectrum of a chemical substance 10 contained in a transparent chemical tank 8 to determine whether the chemical substance 10 is of normal or abnormal condition, i.e. deviating from the normal or average condition from the point of view of the spectrum of electromagnetic radiation transmitted through the chemical substance 10. A source of electromagnetic radiation, in this case a light source 12 is located below the tank 8. There is a fiber optical line 14 above the tank 8 which is connected via line 16 to a spectrum scanner 18.

Scanner 18 compares the spectrum with respect to a light source through normal and abnormal chemicals, to find the intensity of variation specific wavelengths between them. Comparing the new chemical ($H_2SO_4$) with old chemical ($H_2SO_4$) which has been run through 40 lots, the intensities of some wavelengths listed in Table I as follows:

TABLE I a: 406 nm b: 437 nm c: 487 nm d: 548 nm

Figure 1B:
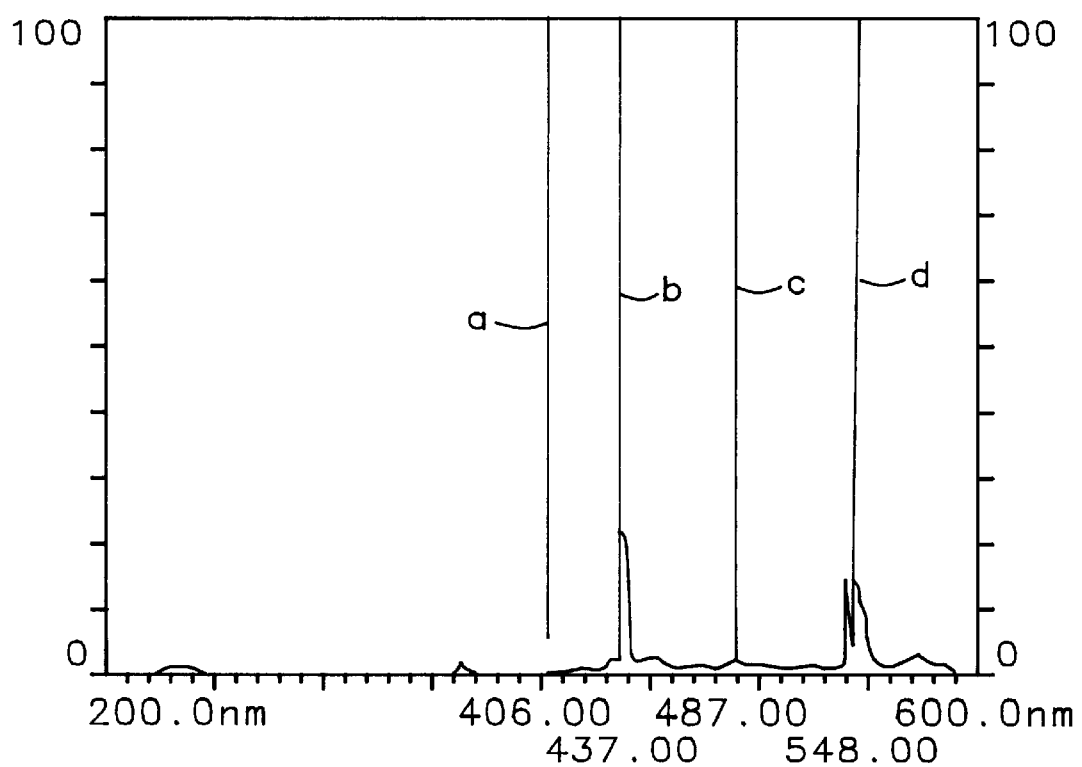
FIGS. 1B and 1C show displays in the spectrum mode for the apparatus of FIG. 1A.
Figure 1C:
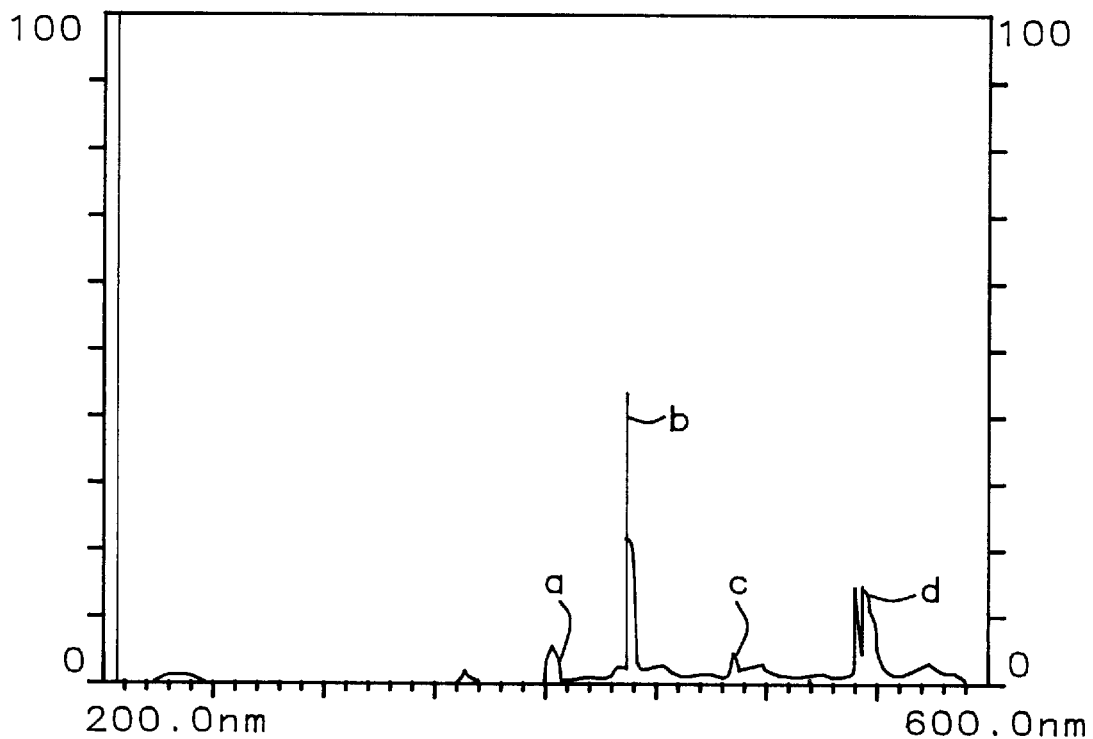

The intensities vary, as seen in FIGS. 1B and 1C where the X axis comprises optical wavelengths of the electromagnetic spectrum from 200.0 nm to 600.0 nm and the Y axis is intensity measured as amplitude percentage (Amp %).

In the case of FIG. 1B, a display is shown in the spectrum mode. The four wavelengths in Table I are marked by lines which extend above the top of the chart. The amplitude is 1.2% and the number of runs equals "0" for the new chemical which is an aqueous solution of sulfuric acid ($H_2SO_4$). The time is 35.7 seconds which means the scanning time of the spectrum referred to the $H_2SO_4$ runs is 35.7 sec.

Gain is 4,1 which means "4" is the working coarse gain for the spectrum intensity and "1" is the working fine gain for the spectrum intensity. HV is 660 Volts, which means the working high voltage set for spectrum intensity and 660 Volts is the standard setting suggested by the operations guide. Line is 548.0 nm, which is the chosen wavelength referred to the amplitude of intensity (1.2%), is 548 nm. In FIG. 1B, there are zoom percentages of ZX1 and ZX5 ZX1 ZY5, ZX1 means the zoom percentage is 100% in the X axis direction. ZY5 means the zoom percentage is 500% in the Y axis direction.

In the case of FIG. 1C, a display is shown in the spectrum mode. The data at the four wavelengths in Table I are marked a, b, c, d but are shorter than in FIG. 1B. The amplitude is 0.0% which is less than the amplitude of 1.2% in FIG. 1B.

The number of runs again equals "0" for the new chemical which is an aqueous solution of sulfuric acid ($H_2SO_4$). The time is again 35.7 seconds. Gain is again 4,1 and HV is again 660 Volts as above. Line is only 206.0 nm as compared with 548.0 nm, which means that there are no specific wavelengths chosen for the purpose of showing the four peaks a, b, c, d clearly. ZX1 ZY5 is as above.

Figure 2A:
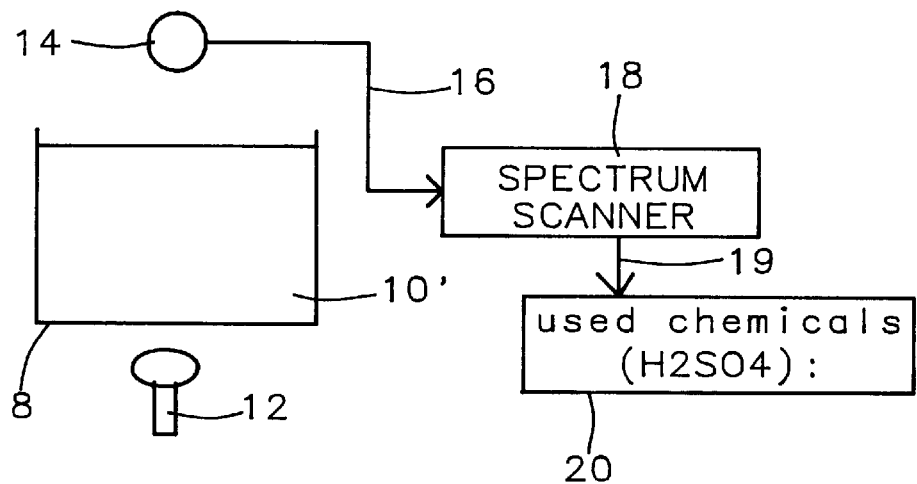
FIG. 2A shows similar apparatus to that in FIG. 1A for measuring the optical spectrum of a different chemical substance.

FIG. 2A shows similar apparatus to that in FIG. 1A for measuring the optical spectrum of a different chemical substance 10' contained in a transparent chemical tank 8 to determine whether the chemical substance 10' is of normal or abnormal condition, i.e. deviating from the normal or average condition from the point of view of the spectrum of electromagnetic radiation transmitted through the chemical substance 10'. A source of electromagnetic radiation, in this case a light source 12 is located below the tank 8. There is a fiber optical line 14 above the tank 8 which is connected via line 16 to a spectrum scanner 18. The output of the spectrum scanner 18 is connected via line 19 to block 20 marked "used chemical ($H_2SO_4$)" which has been through runs of 40 lots.

Figure 2B:
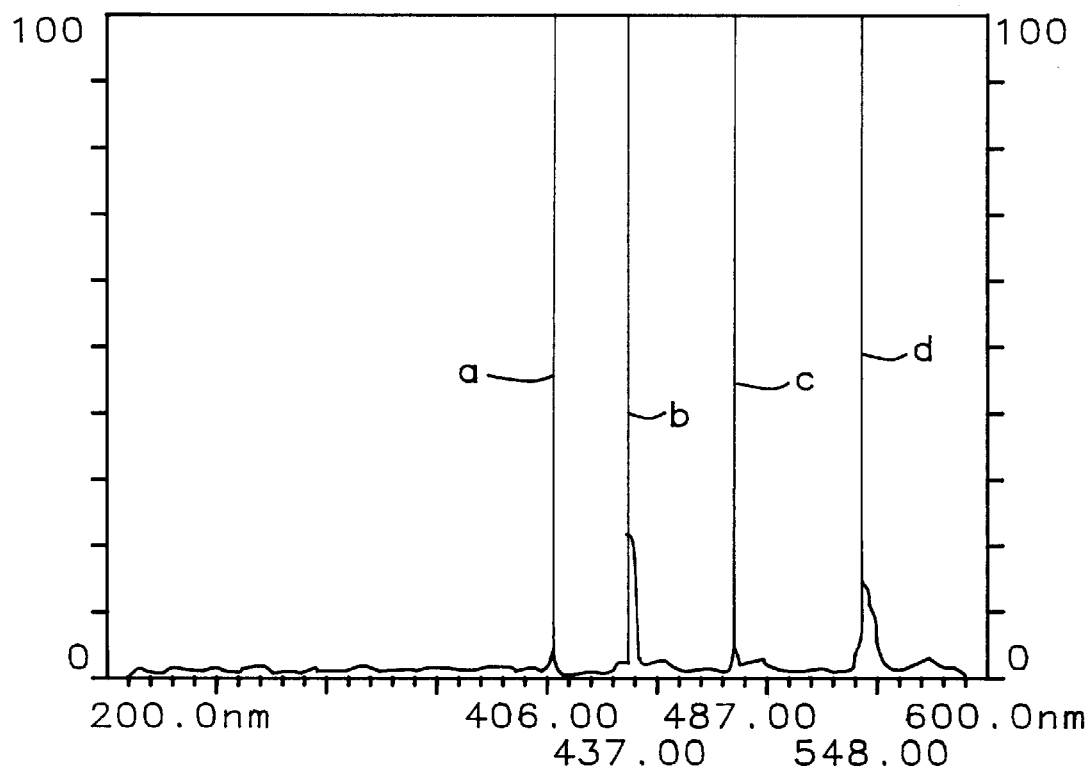
FIGS. 2B and 2C show displays in the spectrum mode for the apparatus of FIG. 2A.

In the case of FIG. 2B, a display is shown in the spectrum mode. The four wavelengths in Table I are marked by lines which extend above the top of the chart. The amplitude is 0.4% and the number of runs equals "40" for the used chemical which is an aqueous solution of sulfuric acid ($H_2SO_4$). The time is 29.5 seconds which means the current scanning time of the spectrum referred to the $H_2SO_4$ 80 runs is 29.5 seconds. The time is less than the 35.7 seconds. in FIGS. 1B and 1C, which means shorter scanning time only. Gain is 4,1; HV is 660 Volts; Line is 548.0 nm; and ZX1 ZY5 are as explained above.

Figure 2C:
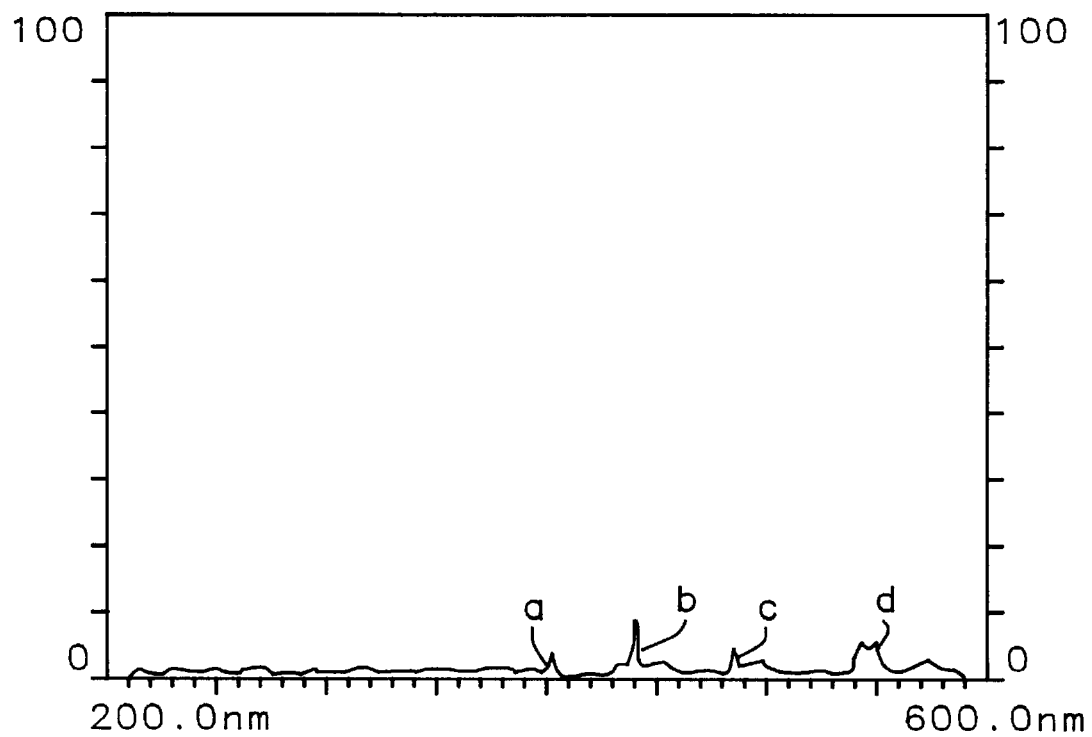

In the case of FIG. 2C, a display is shown in the spectrum mode. The data at the four wavelengths in Table I are marked a, b, c, d but are shorter than in FIG. 2B. The amplitude is 0.0% which is less than the amplitude of 0.4% in FIG. 2B. The number of runs again equals "40" for the new chemical which is an aqueous solution of sulfuric acid ($H_2SO_4$). The time is again 29.5 seconds.

Gain is 4,1, HV is 660 Volts, and ZX1 ZY5, are as explained above, whereas in this case, Line is only 206.0 nm as compared with 548.0 nm.

It should be noted that the solution 10' in FIG. 2A is far more opaque than the solution 10 in FIG. 1A because something remained in 10' after 80 runs.

Referring to FIGS. 3A and 3B, the light source 12 and the tank are similar to FIGS. 1A and 2A and they contain normal (new) chemical solution 20 and abnormal (used) chemical solution 20' respectively. The photosensor 34 is connected via lines 38 and 37 between spectrum or alarm circuits 40 and ground. Suitable photo-sensors 34 are used with sensitivities at wavelengths which indicate that a chemical change timing or alarm point has been reached. As an example of an embodiment of this aspect of the invention, FIGS. 3A and 3B show a photo-sensor 34 which includes a 437 nm passband filter.

FIG. 3B shows photo-sensor 34 darkened by the intensity of abnormal chemical drop to the trigger point of the chemical change timing or alarm function because of the opaque nature of the old chemical solution 20'.

FIGS. 4A and 4B show alternative kinds of photosensors and light source assemblies.

FIG. 4A shows a chemical tank 8 containing a solution 60, in which an assembly 66 is housed with a light source 42 and a photosensor 44. The fluid flow between the light source 42 and the photo-sensor 44 in an assembly which includes the light source and the sensor.

FIG. 4B shows a chemical tank 8 containing a solution 60', in which is located a light source 52 at the bottom of the tank in the solution and a photosensor 54 at the surface of the solution 60' in the solution.

Structures of alternative types of assemblies which can be used in the arrangements such as FIGS. 4A and 4B are shown in FIGS. 4C and 4D.

In FIG. 4C, an assembly 80 includes a transparent conduit (pipe) 82 having a coaxial passageway 81 therethrough for carrying a fluid flowing as indicated by the arrow. Housed within the walls of the conduit 82 on opposite sides of the passageway 81 are a light source LS1 and a photosensor PS1 which aligned so that the light reaching the sensor PS1 is a function of the opacity or tranmissivity of the fluid flowing through the passageway 81.

In FIG. 4D, an assembly 90 includes a transparent body 92 having a passageway 91 therethrough for carrying a fluid flowing as indicated by the arrow. Housed within the walls of the body 92 on opposite sides of the passageway 91 are a light source LS2 and a photosensor PS2 which are aligned so that the light reaching the sensor PS2 is a function of the opacity or tranmissivity of the fluid flowing through the passageway 91.

FIGS. 5A and 5B show photosensors for different kinds of wavelengths.

FIG. 5A shows a chemical tank 8 containing a solution 70, housing an assembly 66 with a light source 62 and a wavelength adjustable photosensor 64, such as a monochromator. Conventional electronics comprising spectrum and endpoint control apparatus are employed.

FIG. 5B shows a chemical tank 8 containing a solution 70', housing an assembly 76 with a light source 72 and a multiple wavelength adjustable photosensor 74. With a set of specific wavelength filters it is possible to choose any one of the wavelengths to be a working channel or any combination the wavelengths.

SUMMARY

This invention provides the advantages as follows:
1. Real-time monitoring of reacting chemicals.
2. Spectrum analysis of new and used chemicals.
3. Use of selected photo-sensors and similar assemblies.

The real time monitor can be used in wet etching, cleaning or semiconductor related process equipment. Apparatus in accordance with this invention can be put inside or outside a treatment tank or used in any way possible to generate a signal to provide an alarm indicating abnormality of the optical characteristics of the chemical being processed.

While this invention has been described in terms of the above specific embodiment(s), those skilled in the art will recognize that the invention can be practiced with modifications within the spirit and scope of the appended claims, i.e. that changes can be made in form and detail, without departing from the spirit and scope of the invention. Accordingly all such changes come within the purview of the present invention and the invention encompasses the subject matter of the claims which follow.

Having thus described the invention, what is claimed as new and desirable to be secured by Letters Patent is as follows:

1. A method for monitoring and controlling a chemical process comprising:
   placing a chemical substance in a chamber adapted for use in treatment of semiconductor devices,
   transmitting an electromagnetic energy from a source at a first location through said chemical substance in said chamber,
   sensing said electromagnetic energy transmitted through said chemical substance from said first location through space within said chamber containing said chemical substance to a second location across said chamber from said first location,
   said sensing being provided with a wavelength adjustable photosensor, and
   comparing the result of said sensing with a standard by performing comparison of the spectrum of transmission of electromagnetic radiation through normal and abnormal chemicals.

2. A method in accordance with claim 1 wherein:
   said sensing is provided with a photosensor positioned across said chamber from said source.

3. A method in accordance with claim 1 wherein:
   said chemical substance comprises a fluid, and
   said source of electromagnetic energy being housed within the walls of a transparent body including a passageway for fluid between said source and said photosensor.

4. A method in accordance with claim 1 wherein:
   said sensing is provided with a wavelength adjustable photosensor and a passband filter between said source and said photosensor.

5. A method in accordance with claim 1 wherein:
   said sensing is provided with a multiple wavelength photosensor.

6. A method in accordance with claim 1 wherein:
   said sensing is provided with a multiple wavelength photosensor and a passband filter between said source and said photosensor.

7. A method in accordance with claim 1 wherein:
   said chemical substance comprises an aqueous solution of sulfuric acid, and
   said sensing is provided with a multiple wavelength photosensor.

8. A method for monitoring and controlling a chemical process comprising:
   placing a chemical solution adapted for use in treatment of semiconductor devices in a chamber adapted for use in treatment of semiconductor devices,
   transmitting an electromagnetic energy from a source located within said chamber through said chemical solution,
   sensing said electromagnetic energy transmitted through said chemical solution with a wavelength adjustable photosensor located within said chamber, and
   comparing the result of said sensing with a standard to determine a value selected from the group consisting of opacity and tranmissivity of said chemical solution, said comparing comprising performing comparison of the spectrum of transmission of electromagnetic radiation through normal and abnormal chemicals.

9. Apparatus for monitoring and controlling a chemical process with a chemical substance adapted for use in treatment of semiconductor devices in a chamber comprising:
   means for transmitting an electromagnetic energy from a source through said chemical substance adapted for use in treatment of semiconductor devices in said chamber,
   means for sensing said electromagnetic energy transmitted through said chemical substance in said chamber, and
   means for comparing the result of said sensing with a standard by performing comparison of the spectrum of transmission of electromagnetic radiation through normal and abnormal chemicals with spectrum analysis apparatus.

10. Apparatus in accordance with claim 9 wherein:

said source of electromagnetic energy and said sensor being housed within the walls of a transparent body which include a passageway for fluid between said source and said photosensor, and a passband filter between said source and said photosensor.

11. Apparatus in accordance with claim 9 wherein:

said means for sensing comprises a multiple wavelength photosensor.

12. Apparatus for monitoring and controlling a chemical process comprising:

a chemical solution adapted for use in treatment of semiconductor devices contained in a chamber adapted for use in treatment of semiconductor devices, means for transmitting electromagnetic energy from a source located within said chamber through said chemical solution, means for sensing said electromagnetic energy transmitted through said chemical solution with a sensor comprising a monochromator located within said chamber, and said means for comparing employs comparison of the spectrum of transmission of electromagnetic radiation through normal and abnormal chemical solutions which spectrum is sensed by said means for sensing with a standard to determine a value selected from the group consisting of opacity and tranmissivity of said chemical substance by employing spectrum analysis.

* * * * *